United States Patent [19]
Peinecke et al.

[11] Patent Number: 5,996,394
[45] Date of Patent: Dec. 7, 1999

[54] GAS METER CALIBRATION DEVICE FOR HYDROGEN-OXYGEN MIXTURES

[75] Inventors: Volker Peinecke; Paul Mohr, both of Stuttgart, Germany

[73] Assignee: Deutsche Forschungsanstalt fuer Luft- und Raumfahrt e. V., Bonn, Germany

[21] Appl. No.: 08/965,223

[22] Filed: Nov. 6, 1997

[30] Foreign Application Priority Data

Nov. 6, 1996 [DE] Germany .............................. 196 45 695

[51] Int. Cl.$^6$ .................................................. G01N 33/00
[52] U.S. Cl. .............................................................. 73/1.03
[58] Field of Search ................................. 73/1.02–1.06

[56] References Cited

U.S. PATENT DOCUMENTS

| | | | |
|---|---|---|---|
| 3,290,920 | 12/1966 | Novak | 73/1.03 |
| 4,385,910 | 5/1983 | Eilers et al. | 73/1.04 |
| 4,498,496 | 2/1985 | Barcellona et al. | 73/1.05 |
| 5,239,856 | 8/1993 | Mettes et al. | 73/1.05 |
| 5,261,452 | 11/1993 | McAndrew et al. | 73/1.03 |
| 5,524,473 | 6/1996 | Haskell | 73/1.03 |

FOREIGN PATENT DOCUMENTS

| | | |
|---|---|---|
| 26 34 496 | 2/1978 | Germany . |
| 28 23 604 | 12/1978 | Germany . |
| 42 38 011 | 5/1994 | Germany . |

OTHER PUBLICATIONS

Hengstenberg et al. *Messen Steuren und Regeln in der Chemischen Technik,* vol. II, Chapter 14, 1980.
Staab, J. "Industrielle Gasanalyse", *tm–Technisches Messen,* 61, 1994.

*Primary Examiner*—Robert Raevis
*Attorney, Agent, or Firm*—Barry R. Lipsitz; Ralph F. Hoppin

[57] ABSTRACT

In order to provide a gas meter calibration device for hydrogen-oxygen mixtures which comprises a connection for a gas meter such that it enables a gas meter for hydrogen-oxygen mixtures to be accurately calibrated, it is proposed that a hydrogen-oxygen mixture can be produced in a mixing zone with oxygen from an oxygen gas store and hydrogen from a hydrogen gas store, and that the composition of the hydrogen-oxygen mixture can be adjusted by means of at least one mass flow regulator, with a control system checking and ensuring that the foreign gas concentration of hydrogen or oxygen in the mixture lies below the lower explosion limit.

20 Claims, 2 Drawing Sheets

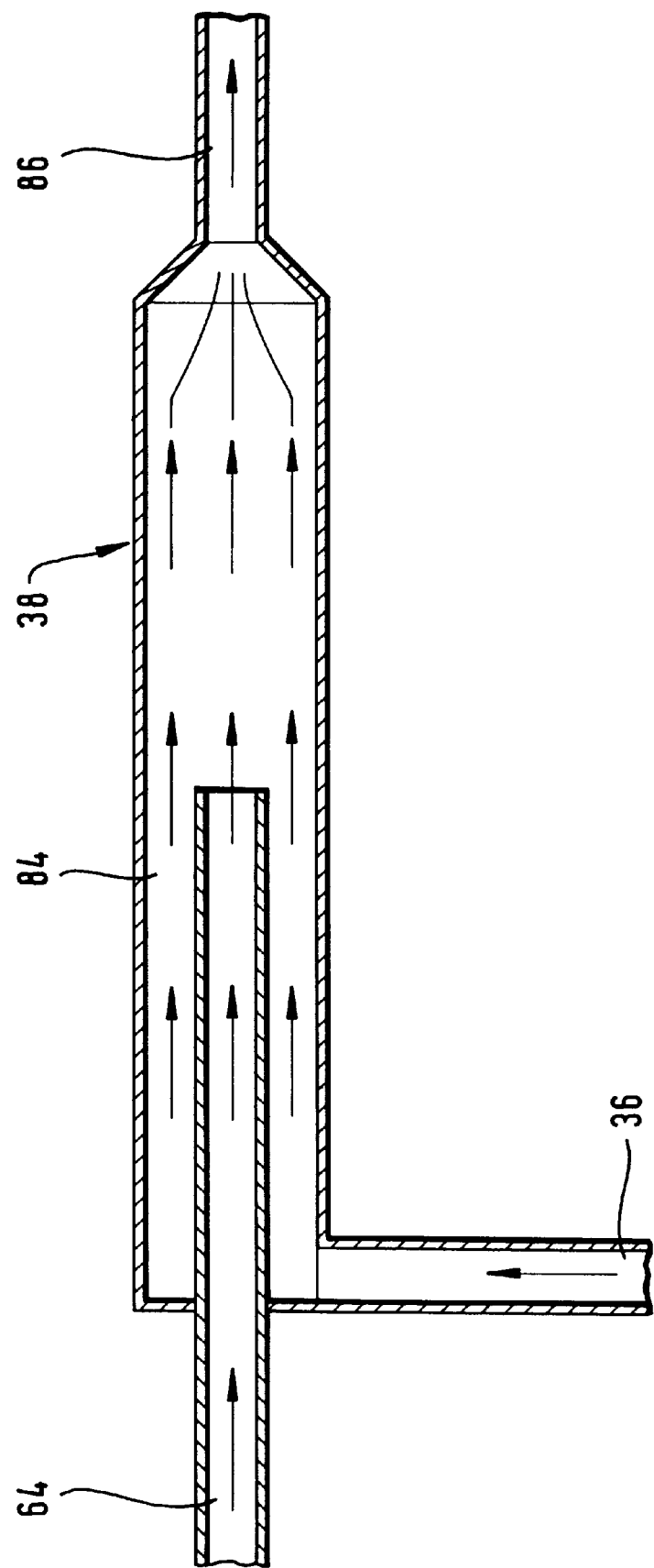

GAS METER CALIBRATION DEVICE FOR HYDROGEN-OXYGEN MIXTURES

BACKGROUND OF THE INVENTION

The invention relates to a gas meter calibration device for hydrogen-oxygen mixtures which comprises a connection for a gas meter.

In plants in which hydrogen or oxygen is produced, such as, for example, in water electrolysis plants, the oxygen gas resulting must constantly be monitored for contamination by hydrogen and the hydrogen gas resulting must constantly be monitored for contamination by oxygen so as to prevent the danger of explosion. It is known that the lower explosion limit for hydrogen-oxygen mixtures lies in the range of approximately 4% by volume of contaminant gas. This applies both to hydrogen contaminants in oxygen and oxygen contaminants in hydrogen. This monitoring process is carried out with the aid of gas meters.

The gas meters must operate accurately to prevent all danger of explosion. These meters must be accurately calibrated to achieve this.

In a known calibration method a gas meter is supplied with a gas mixture in which the hydrogen or the oxygen component is replaced by an inert gas, for example nitrogen. By replacing a component by inert gas, this calibration mixture itself is safeguarded against any danger of explosion.

Since, however, the inert gas has physical properties different to those of the replaced hydrogen or oxygen gas, the properties of the inert gas calibration mixture must be translated to a hydrogen-oxygen mixture. This method thereby becomes inaccurate, as the reverse calculation always entails uncertainties. It is therefore impossible to accurately calibrate a gas meter for hydrogen-oxygen mixtures using this method.

Another known calibration method employs hydrogen-oxygen calibration gases which are already fully premixed and are supplied in gas bottles. This is highly complex, as a large number of gas mixtures of differing compositions are required to accurately calibrate a gas meter. This method therefore gives rise to high expenditure. Moreover, for safety reasons the hydrogen-oxygen gas mixtures which are available have concentrations of the respective foreign gas of a maximum of approximately 1.5% by volume in order to definitely remain below the lower explosion limit. This means that gas meters can only be calibrated over a narrow range.

SUMMARY OF THE INVENTION

The object of the invention is therefore to provide a device of the type according to the preamble which enables a gas meter for hydrogen-oxygen mixtures to be accurately calibrated.

This object is solved according to the invention with respect to a device of the type initially described in that a hydrogen-oxygen mixture can be produced in a mixing zone with oxygen from an oxygen gas store or supply and hydrogen from a hydrogen gas store or supply, and that the composition of the hydrogen-oxygen mixture can be adjusted by means of at least one mass flow regulator, with a control system checking and ensuring that the foreign gas concentration of hydrogen or oxygen in the mixture (i.e. the concentration of the minority gas) lies below the lower explosion limit.

The device according to the invention enables hydrogen-oxygen mixtures to be produced in any composition which lies below the lower explosion limit, so that a gas meter can be accurately calibrated.

As mass flow regulators operate with a high degree of accuracy, the composition of the mixture can be accurately adjusted. This ensures that the mixture is of the composition required to calibrate the gas meter and that no explosive mixture can be produced.

Different mixture compositions can easily be produced if required.

It is advantageous if the foreign gas concentration of hydrogen or oxygen in the mixture can be adjusted by means of one mass flow regulator for the foreign gas and by means of one mass flow regulator for the oxygen or hydrogen carrier gas. The respective mass flows can thereby be accurately controlled and the concentration of foreign gas in the mixture accurately adjusted.

For this purpose it is also advantageous if the sum of the flow through the mass flow regulator for the foreign gas and the flow through the mass flow regulator for the carrier gas is maintained constant by the control system, so that the percentage by volume of foreign gas and carrier gas in the mixture can be easily and accurately adjusted, thus ensuring that the gas mixture lies below the lower explosion limit with a sufficient safety margin.

In an advantageous embodiment of the device according to the invention the total flow lies in the range between 80 Nl/h and 120 Nl/h.

The total flow is preferably 100 Nl/h, so that the composition of the mixture can easily be adjusted and monitored.

The maximum concentration of foreign gas in the carrier gas which can be set may in this case be lower than 3.5% by volume, thus giving a safety margin of at least 0.5% by volume with respect to the lower explosion limit.

If the maximum concentration of foreign gas in the carrier gas which can be set is lower than 3% by volume, there will be a safety margin of at least 1% by volume with respect to the lower explosion limit.

In a particularly advantageous embodiment the mixing zone is formed as a turbulence zone for effective intermixing of the gases. This achieves effective intermixing of the foreign gas and the carrier gas and makes it impossible for one gas component to build up in the device. The build-up of one gas component entails the risk of an ignitable mixture resulting.

In an advantageous embodiment the mixing zone has a greater cross section than respective lines for feeding the carrier gas and the foreign gas into the mixing zone and a line for removing the hydrogen-oxygen mixture from the mixing zone, so that effective turbulence of the foreign gas and the carrier gas in the mixing zone can be achieved.

The electrolysis hydrogen and electrolysis oxygen resulting, for example, from the electrolysis of water comprise water vapour, and the relative humidity of the electrolysis gases may reach up to 100% at ambient temperature. Therefore, in order to guarantee an accurate indication of the $H_2/O_2$ concentration of a gas meter used for monitoring purposes during electrolysis, the gas meter must be calibrated with a humid calibration mixture. As opposed to this, the methods known from the prior art are based on calibration with a dry, unhumidified calibration gas, so that a significant measuring error may occur when a humid hydrogen-oxygen mixture is fed to a gas meter which is thus calibrated.

Therefore, in order to humidify the hydrogen-oxygen mixture, in a variant of an embodiment according to the invention this mixture can be conveyed through a humidifier, in which the mixture can in particular be saturated with water vapour. The hydrogen-oxygen mixture thereby has a defined moisture content. It is advantageous for the saturation to take place at ambient temperature, i.e. in the range from approximately 15° C. to 20° C. This enables a different degree of saturation with water vapour to be set by cooling the humidified gas mixture to below ambient temperature.

In order to increase operational safety, it is advantageous for the device to comprise a backflash barrier which, related to the gas stream, is disposed after the mixing zone. The backflash barrier serves to prevent backflash and as a flame trap which, in the case of an abnormal occurrence, prevents the gas mixture from backfiring into the region of the mixing zone.

For safety reasons it is of advantage for the device to comprise a shut-off valve which can prevent gas from penetrating into or entering the device. When the shut-off valve is closed while the device is out of operation this measure prevents an ignitable mixture from forming inside the device due to the penetration of hydrogen or oxygen from the outside space.

In an advantageous variant of an embodiment the hydrogen-oxygen mixture can be divided into a first mixture stream and a second mixture stream. This enables a gas meter to be fed with a volumetric flow which is independent of the total flow through the device and can be adapted to the specifications of the gas meter.

It is then of particular advantage if the connection for a gas meter is disposed in the first mixture stream and, in particular, the volumetric flow in the first mixture stream is adjustable.

As a result of disposing a cooler, preferably provided with a condenser, for cooling the hydrogen-oxygen mixture in the first mixture stream, the dew point of the humidified gas mixture can be lowered to a predetermined lower temperature. The degree of moisture in the hydrogen-oxygen mixture can thus be adjusted.

In order to increase the operational safety of the plant, it is of particular advantage if nitrogen can be introduced into a carrier gas line and a foreign gas line from a nitrogen gas store. The nitrogen is used for producing an inert atmosphere, so that nitrogen can be fed in if operational disturbances occur to prevent an explosive hydrogen-oxygen mixture from resulting. The nitrogen may also be used to render the device inert when the plant is out of operation.

In an advantageous embodiment the device comprises a gas path for producing a hydrogen-oxygen mixture with hydrogen as the foreign gas and oxygen as the carrier gas and a gas path for producing a mixture with oxygen as the foreign gas and hydrogen as the carrier gas. The device can therefore simultaneously be used for calibrating a gas meter which serves to monitor the foreign gas concentration of hydrogen in oxygen gas and for calibrating a gas meter which serves to monitor the oxygen concentration in hydrogen as the carrier gas.

A predetermined fixed and constant pressure for the foreign gas stream and the carrier gas stream, which is necessary for accurate adjustment of the composition of a hydrogen-oxygen mixture, can be achieved by disposing a pressure reducing unit downstream of both the hydrogen gas store and the oxygen gas store to reduce the pressure of the gases coming from the hydrogen gas store and the oxygen gas store to a predetermined pressure.

In order to increase the safety of the device according to the invention, it is particularly advantageous for a carrier gas feed and a foreign gas feed in the mixing zone to each comprise a shutoff valve. Should a disturbance occur, it is thus possible to prevent gas from being fed into the mixing zone and thus the development of an explosive mixture in this zone.

BRIEF DESCRIPTION OF THE DRAWINGS

FIG. 1 is a diagrammatic view of an embodiment of a device according to the invention and FIG. 2 is an embodiment of a mixing zone.

DETAILED DESCRIPTION OF THE INVENTION

Figure 1:
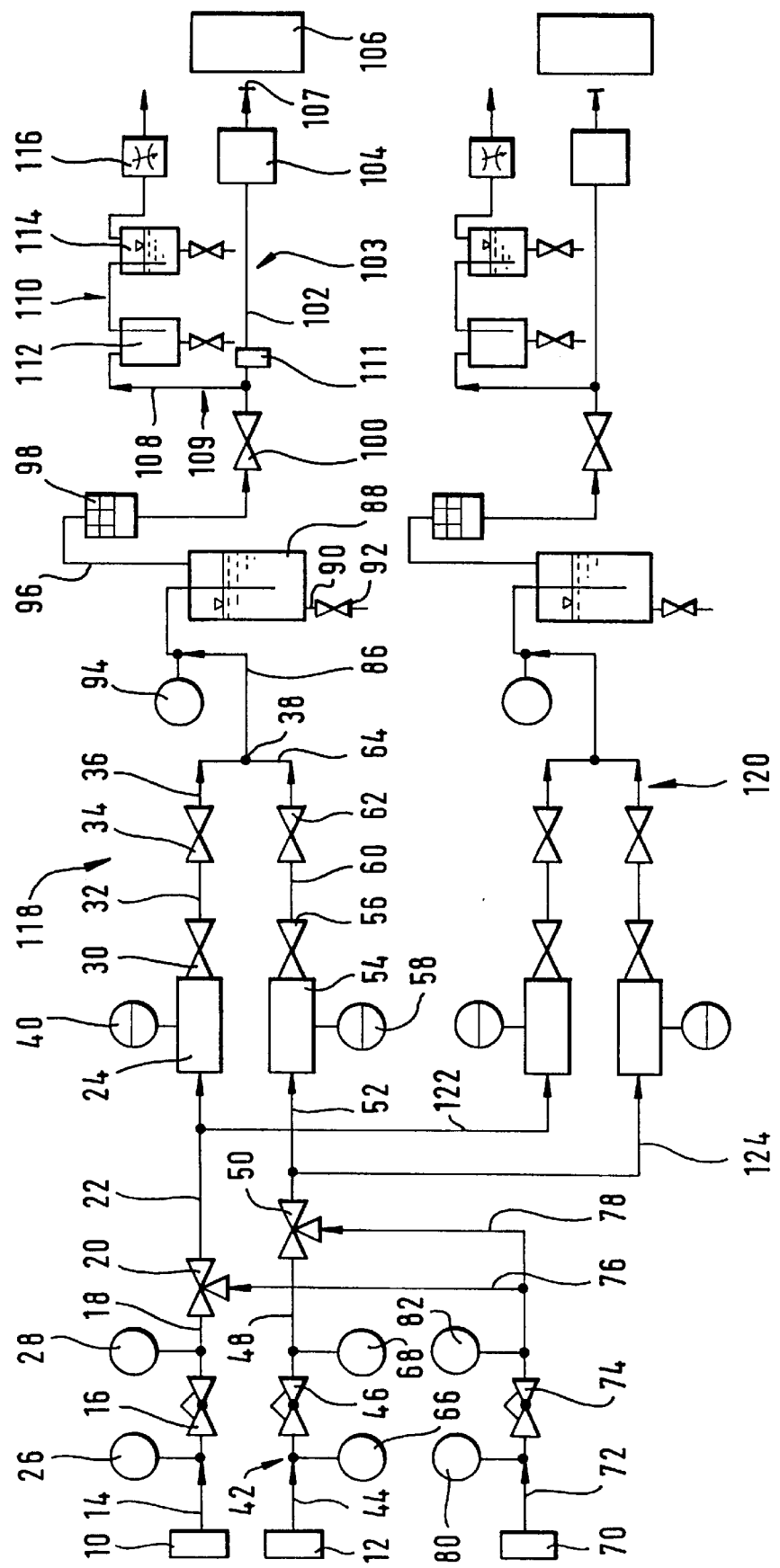

As shown in FIG. 1, an embodiment of a device according to the invention comprises an oxygen gas store or reservoir 10, which may in particular be an oxygen pressure bottle, and a hydrogen gas store or reservoir 12, which may be a hydrogen pressure bottle. A line 14 leads from the oxygen gas store 10 to an inlet of a pressure reducing unit 16, which may in particular be of the two-stage type, and a line 18 leads from an outlet of the pressure reducing unit 16 to a first inlet of a three-way valve 20. A line 22 leads from an outlet of the three-way valve 20 to an inlet of a mass flow regulator 24.

A pressure sensor 26 for measuring the pressure of the oxygen coming from the oxygen gas store 10 is disposed in the line 14. A pressure regulator (not shown in the figure) controls the pressure reducing unit 16 so that the oxygen gas coming from the pressure reducing unit 16 is at a fixed and constant pressure, which is monitored by means of a pressure sensor 28 in the line 18.

The mass flow regulator 24 is provided with a valve 30, and a line 32 leads from an outlet of the valve 30 to an inlet of a shutoff valve 34. A line 36 leads from an outlet of the shutoff valve 34 into a mixing zone 38.

The mass flow through the mass flow regulator 24 can be controlled by way of a control unit 40.

In a hydrogen gas path 42 a line 44 leads from the hydrogen gas store 12 to an inlet of a pressure reducing unit 46 and a line 48 leads from an outlet of this pressure reducing unit 46, which may in particular be formed as a two-stage pressure reducer, to a first inlet of a three-way valve 50. A line 52 leads from an outlet of the three-way valve 50 to a mass flow regulator 54 for hydrogen, which regulator comprises a valve 56 and the mass flow through which is controlled by means of a control unit 58.

A line 60 leads from an outlet of the valve 56 to an inlet of a shutoff valve 62 and a line 64 leads from an outlet of the shutoff valve 62 into the mixing zone 38.

A pressure sensor 66 in the line 44 records the pressure of the hydrogen flowing from the hydrogen gas store 12 in the line 44, and a pressure sensor 68 in the line 48 is used to check that hydrogen gas is fed to the mass flow regulator 54 through the pressure reducing unit 46 at a fixed, predetermined pressure.

A line 72 leads from a nitrogen gas store 70 to an inlet of a pressure reducing unit 74, a line 76 leads from an outlet of the pressure reducing unit 74 into a second inlet of the three-way valve 20 and a line 78 leads from this outlet to a second inlet of the three-way valve 50. The pressure of the nitrogen in the lines 76 and 78 is adjusted to a fixed predetermined value by means of a pressure sensor 80, which is disposed in the line 72, and a pressure sensor 82, which monitors the pressure of the nitrogen flowing out of the pressure reducing unit 74. This value is advantageously slightly greater than the value which is predetermined for the hydrogen and the oxygen.

The feed line 36 for oxygen gas and the feed line 64 for hydrogen gas lead into the mixing zone 38. In a variant of an embodiment (FIG. 2) the mixing zone is formed by a line section 84 which has a greater diameter than both the lines 36 and 64. At one end of the line section 84 the line 36 for oxygen gas and the line 64 for hydrogen gas open out in a central region of the line section 84, so that hydrogen gas can flow into the oxygen gas stream and effective turbulence of the two gases is achieved.

At another end of the line section 84 the latter narrows into a line 86, through which the hydrogen-oxygen gas mixture which has resulted in the mixing zone 38 and in which oxygen is the carrier gas and hydrogen the foreign gas is removed.

The gas mixture is fed to a humidifier 88 through the line 86. This humidifier comprises a storage vessel with distilled water. Water can be fed to the humidifier 88 or removed from the latter by way of a line 90 comprising a shutoff valve 92.

A pressure sensor 94 for monitoring the pressure in the hydrogen-oxygen mixture is disposed in the line 86.

A line 96 conveys the hydrogen-oxygen mixture which is humidified in the humidifier 88 via a backflash barrier 98 to an inlet of a shutoff valve 100. The backflash barrier 98 prevents the hydrogen-oxygen mixture from backfiring into the line 96 in the case of an abnormal occurrence.

A line 102, via which a first mixture stream 103 is branched off, leads from an outlet of the shutoff valve 100 to a cooler 104, which may in particular comprise a condenser and in which the humidified mixture is cooled to a dew point which is lower than the temperature at which the mixture is humidified in the humidifier 88. The gas mixture leaving the cooler is fed to a gas meter 106 for the calibration thereof. For this purpose the first mixture stream has a connection 107 for a gas meter 106.

In a variant of an embodiment the first mixture stream 103 has a flow regulator 111 by means of which the flow of mixture can be adjusted. The flow regulator 111 is preferably disposed before the cooler 104.

A second mixture stream 109 is branched off from the line 102 by means of a bypass line 108, this stream 109 being fed to a safety immersion system 110 comprising a first plastics pipe 112, through which the second mixture stream 109 flows, and a second plastics pipe 114, which is filled with water and through which the second mixture stream 109 must also pass. At its outlet side the bypass line 108 comprises a needle valve 116, by means of which an overpressure in the line 108 can be adjusted.

In a variant of an embodiment the device comprises—in addition to a gas path 118 which, as described above, serves to produce a hydrogen-oxygen mixture with oxygen as the carrier gas and hydrogen as the foreign gas—a gas path 120 which serves to produce a hydrogen-oxygen mixture with hydrogen as the carrier gas and oxygen as the foreign gas. The arrangement of the gas path 120 is the same as that for the gas path 118, with a line 122 being branched off the line 22 and leading to a mass flow regulator for oxygen and a line 124 being branched off the hydrogen line 52 and leading to a mass flow regulator for hydrogen.

The device operates as follows:

Pure oxygen or hydrogen—the purity of the two gases being at least 99.995% in each case—is fed from the oxygen gas store 10 or the hydrogen gas store 12 to the pressure reducing unit 16 or 46, in order to reduce the gas pressure from the storage pressure to a pressure of, for example, 10 bar with a high degree of accuracy. The gases flow to the mass flow regulators 40 and 54. The total mass flow through the two regulators 24 and 54 is maintained constant, for example at a nominal flow of 100 Nl/h. As the nominal flow through the calibration device is defined for standard conditions, the nominal flow represents a mass flow.

Each of the regulators 24 and 54 operates with a relative flow accuracy which, related to the nominal flow, is better than approximately 1%. If 100 Nl/h is set as the total flow, the nominal flow in the regulator 24 is also 100 Nl/h for the carrier gas. In order to achieve a sufficient safety margin with respect to the lower explosion limit of a foreign gas content of 4% by volume, the maximum foreign gas concentration which can be set is preferably 3% by volume. In this case the nominal flow in the mass regulator for the foreign gas is then 3 Nl/h. The overall result of this is that the effects of inaccuracies of the mass flow regulators 24 and 54 are not such as to enable the lower explosion limit for a hydrogen-oxygen mixture to be reached.

Should a foreign gas concentration of x % by volume be set, a mass flow of (100−x) Nl/h is then set at the carrier gas mass flow regulator 24 and a flow of x Nl/h at the foreign gas mass flow regulator 54.

The foreign gas is mixed with the carrier gas in the mixing zone 38, with provision being made for effective turbulence, so that there is no possibility of a build-up of one gas in the mixing zone 38.

This gas mixture is conveyed through the humidifier 88, in which the mixture is saturated with water vapour, preferably at ambient temperature. The humidified gas mixture is divided into the first mixture stream 103 and the second mixture stream 109, and the first mixture stream 103 passes through the cooler 104, in which the dew point of the gas mixture is lowered to a defined lower temperature as ambient temperature, for example 4° C. This gas stream can then be used to calibrate a gas meter 106.

The gas stream is divided into the first and the second gas stream in order to feed to the gas meter 106 a gas mass stream which is suitable for the meter. The excess proportion of the total stream is removed by the second mixture stream 109 in the bypass line 108.

The shutoff valve 100 is closed when the plant is out of operation, so that no gas can penetrate the device from the outside space. The shutoff valves 34 and 62 are also closed in order to prevent the development of an ignitable mixture in the device. When the plant is out of operation the device is also rendered inert by nitrogen from the nitrogen gas store 70, so as likewise to prevent the development of an explosive mixture.

Should there be an abnormal occurrence, the plant may be rendered inert by means of nitrogen in order to prevent the development of an explosive mixture. For this purpose nitrogen is injected via the second inlet of the three-way valve 20 or the three-way valve 50 into the lines 22 and 52 and the feed of carrier gas and foreign gas into these lines is simultaneously interrupted by means of the three-way valves.

What is claimed is:

1. A gas meter calibration device for hydrogen-oxygen mixtures, comprising:

a connection for a gas meter, a mixing zone wherein a hydrogen-oxygen mixture is produced with oxygen from an oxygen gas store, and hydrogen from a hydrogen gas store, wherein a foreign gas concentration of hydrogen or oxygen in the mixture is adjustable by means of a mass flow regulator for the foreign gas, and by means of a mass flow regulator for the oxygen or hydrogen carrier gas, and a control system for checking and ensuring that the foreign gas concentration of hydrogen or oxygen in the mixture lies below a lower explosion limit, wherein said control system maintains the sum of the flow through the mass flow regulator for the foreign gas and the flow through the mass flow regulator for the carrier gas substantially constant.

2. A gas meter calibration device according to claim 1, further comprising:

a respective pressure reducing unit disposed downstream of the hydrogen gas store and/or the oxygen gas store to reduce a pressure of the gases coming from the hydrogen gas store and/or the oxygen gas store to a predetermined pressure.

3. A gas meter calibration device according to claim 1, wherein:

feeds for feeding the carrier gas and the foreign gas into the mixing zone each comprise a shutoff valve.

4. A gas meter calibration device according to claim 1, wherein:

a total flow lies in a range between 80 Nl/h and 120 Nl/h.

5. A gas meter calibration device according to claim 4, wherein:

the total flow is 100 Nl/h.

6. A gas meter calibration device according to claim 1, wherein:

a maximum concentration of foreign gas in the carrier gas, which can be set, is lower than 3.5% by volume.

7. A gas meter calibration device according to claim 1, wherein:

a maximum concentration of foreign gas in the carrier gas, which can be set, is lower than 3% by volume.

8. A gas meter calibration device according to claim 1, wherein:

the mixing zone comprises a turbulence zone for effective intermixing of the gases.

9. A gas meter calibration device according to claim 8, wherein:

the foreign gas flows into a stream of the carrier gas in the mixing zone.

10. A gas meter calibration device according to claim 8, wherein:

the mixing zone has a greater cross section than respective lines for feeding the carrier gas and the foreign gas into the mixing zone, and a line for removing the hydrogen-oxygen mixture from the mixing zone.

11. A gas meter calibration device according to claim 1, further comprising:

a humidifier, through which the hydrogen-oxygen mixture is conveyed.

12. A gas meter calibration device according to claim 11, wherein:

the humidifier is adapted to saturate the mixture with water vapour.

13. A gas meter calibration device according to claim 1, further comprising:

a backflash barrier which, in relation to the gas stream, is disposed after the mixing zone.

14. A gas meter calibration device according to claim 1, further comprising:

a shut-off valve for preventing gas from penetrating into the device.

15. A gas meter calibration device according to claim 1, further comprising:

means for dividing the hydrogen-oxygen mixture into a first mixture stream and a second mixture stream.

16. A gas meter calibration device according to claim 15, wherein:

the connection for the gas meter is disposed in the first mixture stream.

17. A gas meter calibration device according to claim 16, further comprising:

means for adjusting a volumetric flow in the first mixture stream.

18. A gas meter calibration device according to claim 15, further comprising:

a cooler disposed in the first mixture stream for cooling the hydrogen-oxygen mixture.

19. A gas meter calibration device according to claim 1, further comprising:

means for introducing nitrogen from a nitrogen gas store into a carrier gas line for the carrier gas, and into a foreign gas line for the foreign gas.

20. A gas meter calibration device according to claim 1, further comprising at least one of:

a gas path for producing the hydrogen-oxygen mixture with hydrogen as the foreign gas and oxygen as the carrier gas, and a gas path for producing the hydrogen-oxygen mixture with oxygen as the foreign gas and hydrogen as the carrier gas.

* * * * *